(12) United States Patent
Goto et al.

(10) Patent No.: US 10,801,958 B2
(45) Date of Patent: Oct. 13, 2020

(54) OPTICAL SENSOR

(71) Applicants: KOMATSU LTD., Minato-ku, Tokyo (JP); KELK Ltd., Hiratsuka-shi, Kanagawa (JP)

(72) Inventors: Daisuke Goto, Hiratsuka (JP); Tomonori Murata, Hiratsuka (JP); Hirokuni Hachiuma, Hiratsuka (JP); You Sangawa, Tokyo (JP); Ryoji Kasuya, Tokyo (JP); Kazuo Miyabe, Tokyo (JP)

(73) Assignees: KOMATSU LTD., Minato-ku, Tokyo (JP); KELK LTD., Hiratsuka-shi, Kanagawa (JP)

( * ) Notice: Subject to any disclaimer, the term of this patent is extended or adjusted under 35 U.S.C. 154(b) by 0 days.

(21) Appl. No.: 16/092,518

(22) PCT Filed: Apr. 11, 2017

(86) PCT No.: PCT/JP2017/014839
§ 371 (c)(1),
(2) Date: Oct. 10, 2018

(87) PCT Pub. No.: WO2017/187967
PCT Pub. Date: Nov. 2, 2017

(65) Prior Publication Data
US 2019/0128807 A1 May 2, 2019

(30) Foreign Application Priority Data
Apr. 27, 2016 (JP) ................. 2016-089734

(51) Int. Cl.
*G01N 21/59* (2006.01)
*G01N 33/28* (2006.01)

(52) U.S. Cl.
CPC ......... *G01N 21/59* (2013.01); *G01N 33/2888* (2013.01)

(58) Field of Classification Search
CPC ............... G01N 33/2888; G01N 21/59; G01N 33/28–32
See application file for complete search history.

(56) References Cited

U.S. PATENT DOCUMENTS 9,201,054 B2 12/2015 Shirata
2008/0024761 A1 1/2008 Kong et al.
(Continued)

FOREIGN PATENT DOCUMENTS

CN 201425571 Y 3/2010
CN 103149158 A 6/2013
(Continued)

*Primary Examiner* — Hina F Ayub
(74) *Attorney, Agent, or Firm* — Faegre Drinker Biddle & Reath LLP

(57) ABSTRACT

An optical sensor is provided, in which members forming an optical path can be reliably supported without blocking the optical path extending from a light source to a light receiver. An optical sensor includes a light source configured to emit light, and a light receiver configured to receive the light emitted from the light source. An optical path extending from the light source to the light receiver extends through an oil infiltrating space into which oil infiltrates. The optical sensor further includes: a substrate on which the light source is mounted; a substrate on which the light receiver is mounted; a fixing member including an accommodation space in which the substrates are accommodated; and a sealing resin contained in the accommodation space and sealing the substrate.

7 Claims, 16 Drawing Sheets

(56) References Cited

U.S. PATENT DOCUMENTS

| | | | |
|---|---|---|---|
| 2010/0157304 A1* | 6/2010 | Takahashi | F16C 19/52 356/442 |
| 2013/0250281 A1 | 9/2013 | Shirata | |
| 2013/0250303 A1 | 9/2013 | Shirata et al. | |

FOREIGN PATENT DOCUMENTS

| | | | |
|---|---|---|---|
| CN | 105259129 | A | 1/2016 |
| EP | 2 829 864 | A1 | 1/2015 |
| GB | 2492821 | A | 1/2013 |
| JP | S62-238444 | A | 10/1987 |
| JP | H02-118853 | U | 9/1990 |
| JP | H06-102172 | A | 4/1994 |
| JP | H07-146233 | A | 6/1995 |
| JP | H10-104160 | A | 4/1998 |
| JP | 2000-275175 | A | 10/2000 |
| JP | 2000-338041 | A | 12/2000 |
| JP | 2003-168182 | A | 6/2003 |
| JP | 2008-26045 | A | 2/2008 |
| JP | 2008-134136 | A | 6/2008 |
| JP | 2008-139188 | A | 6/2008 |
| JP | 2010-261808 | A | 11/2010 |
| JP | 2012-117951 | A | 6/2012 |
| JP | 2013-195206 | A | 9/2013 |
| JP | 2014-8569 | A | 1/2014 |
| JP | 2015-10934 | A | 1/2015 |
| JP | 5839436 | B2 | 1/2016 |
| JP | 2016-20925 | A | 2/2016 |
| WO | WO-2007-083520 | A1 | 7/2007 |
| WO | WO-2012/074112 | A1 | 6/2012 |

\* cited by examiner

OPTICAL SENSOR

TECHNICAL FIELD

The present invention relates to an optical sensor.

BACKGROUND ART

There is a disclosure related to an optical sensor for detecting deterioration of lubricating oil in a machine. The optical sensor has a conventional configuration including: a first space between a light emitting element configured to emit light and a gap forming member having a gap for oil serving as a gap through which oil infiltrates; and a second space between a light receiving element configured to detect light and the gap forming member. A support member configured to support the light emitting element, the light receiving element and the gap forming member has a surface to which the gap forming member is bonded. On this surface, a groove is formed around an opening of the first space and an opening of the second space (for example, see Japanese Patent No. 5839436 (PTD 1)).

CITATION LIST

Patent Document

PTD 1: Japanese Patent No. 5839436

SUMMARY OF INVENTION

Technical Problem

PTD 1 discloses that an annular groove is provided for preventing an adhesive for fixing the gap forming member to the support member from infiltrating into the first space and the second space. When an excessive amount of an adhesive is applied so as to reliably fix the gap forming member to the support member, the adhesive may overflow into the first space or the second space. The first space and the second space form an optical path extending from the light emitting element to the light receiving element. Thus, there may be a possibility that the adhesive overflowing into the first space or the second space may interfere with the optical path to block the light, thereby deteriorating the detection accuracy of the optical sensor. On the other hand, when the amount of the adhesive is insufficient, there may be possibilities that the strength for fixing the gap forming member to the support member becomes insufficient and that the lubricating oil leaks from between the gap forming member and the support member.

An object of the present invention is to provide an optical sensor in which members constituting an optical path can be reliably supported without blocking the optical path extending from a light emitting element to a light receiving element.

Solution to Problem

An optical sensor of the present invention includes: a light emitting element configured to emit light; and a light receiving element configured to receive the light emitted from the light emitting element. An optical path from the light emitting element to the light receiving element extends through an oil infiltrating space as a space into which oil infiltrates. The optical sensor further includes: a substrate on which one or both of the light emitting element and the light receiving element is or are mounted; an accommodation member including an accommodation space in which the substrate is accommodated; and a sealing resin contained in the accommodation space and sealing the substrate.

Advantageous Effects of Invention

According to the optical sensor of the present invention, members constituting an optical path can be reliably supported without blocking the optical path extending from a light emitting element to a light receiving element.

DESCRIPTION OF EMBODIMENTS

Figure 1:
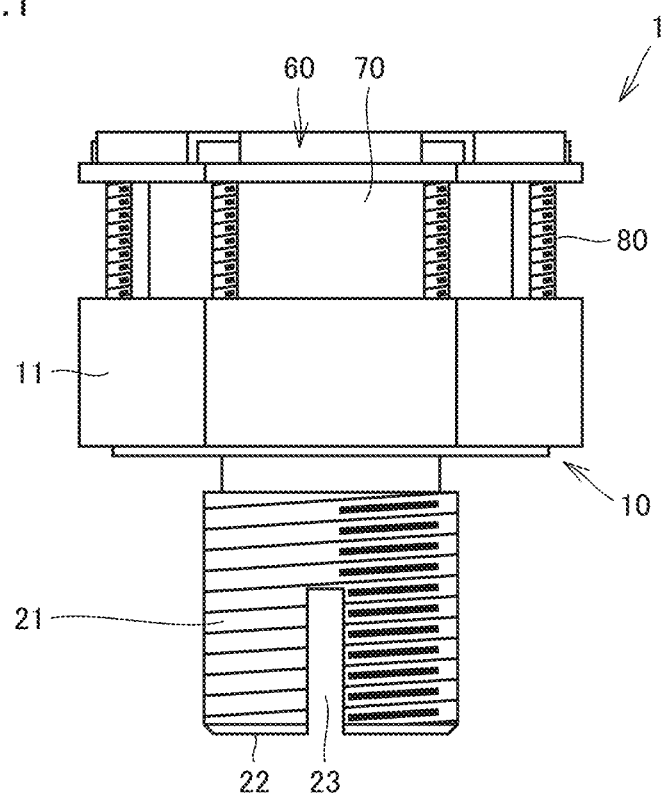
FIG. 1 is a front view of an optical sensor according to the first embodiment.

In the following, an optical sensor according to each of embodiments of the present invention will be described with reference to the accompanying drawings. In the following description, the same components are designated by the same reference characters. Names and functions thereof are also the same. Accordingly, the detailed description thereof will not be repeated.

First Embodiment

FIG. 1 is a front view of an optical sensor 1 according to the first embodiment. Optical sensor 1 serves as an apparatus attached to a machine and configured to detect impurities contained in lubricating oil in the machine. The machine to which optical sensor 1 is attached may be a machine mounted in a work vehicle represented by mining machinery, for example. Optical sensor 1 may be attached, for example, to a gearbox, a transaxle, a hydraulic system, or the like.

As shown in FIG. 1, optical sensor 1 includes a fixing member 10 for fixing optical sensor 1 to the machine. Fixing member 10 has a bolt shape and includes a head portion 11 and a thread portion 21. Head portion 11 has an outer shape formed in a regular hexagonal prism shape. Thread portion 21 has an outer circumferential surface that is threaded. Thread portion 21 has a distal end face 22. Thread portion 21 is provided with a groove formed of a partial recess on distal end face 22. This groove constitutes an oil infiltrating space 23 into which lubricating oil infiltrates.

Optical sensor 1 further includes: a cover member 60 disposed at a distance from head portion 11 of fixing member 10; a heat insulating member 70 disposed between fixing member 10 and cover member 60; and a plurality of bolts 80 configured to integrally couple fixing member 10 and cover member 60.

Fixing member 10 and cover member 60 each are formed of a material with high thermal conductivity, such as metal. Fixing member 10 and cover member 60 may be formed of a steel material or an aluminum alloy, for example. Heat insulating member 70 is formed of a material with low thermal conductivity such as a resin in order to suppress heat transfer between fixing member 10 and cover member 60. Heat insulating member 70 is formed of a material that is lower in thermal conductivity than the material forming fixing member 10 and cover member 60.

Figure 2:
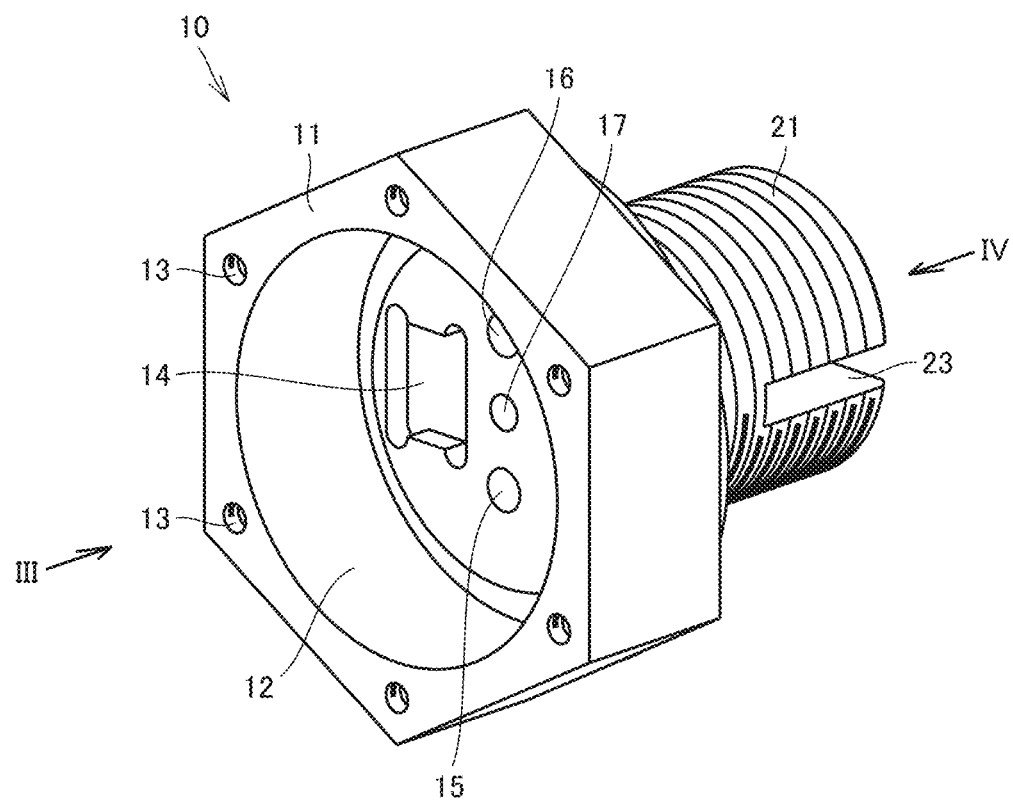
FIG. 2 is a perspective view of a fixing member shown in FIG. 1.
Figure 3:
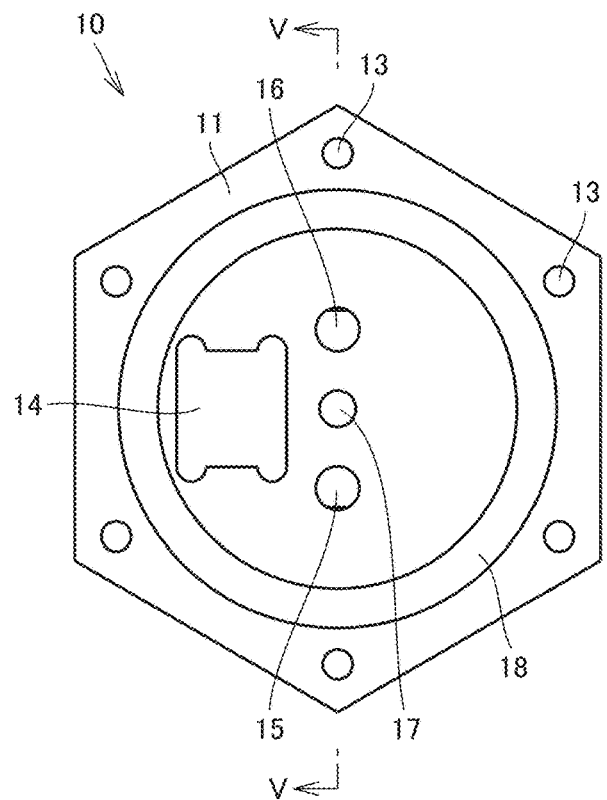
FIG. 3 is an outline diagram of the fixing member as seen from the direction of an arrow III in FIG. 2.
Figure 4:
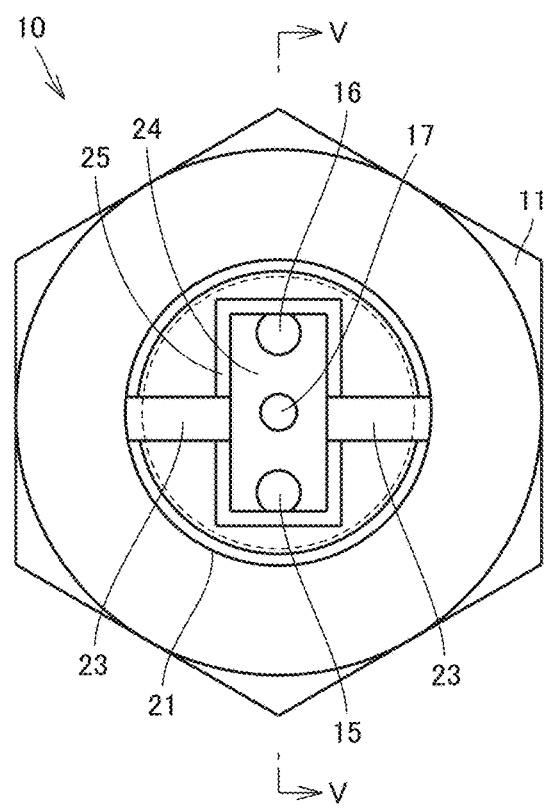
FIG. 4 is an outline diagram of the fixing member as seen from the direction of an arrow IV in FIG. 2.
Figure 5:
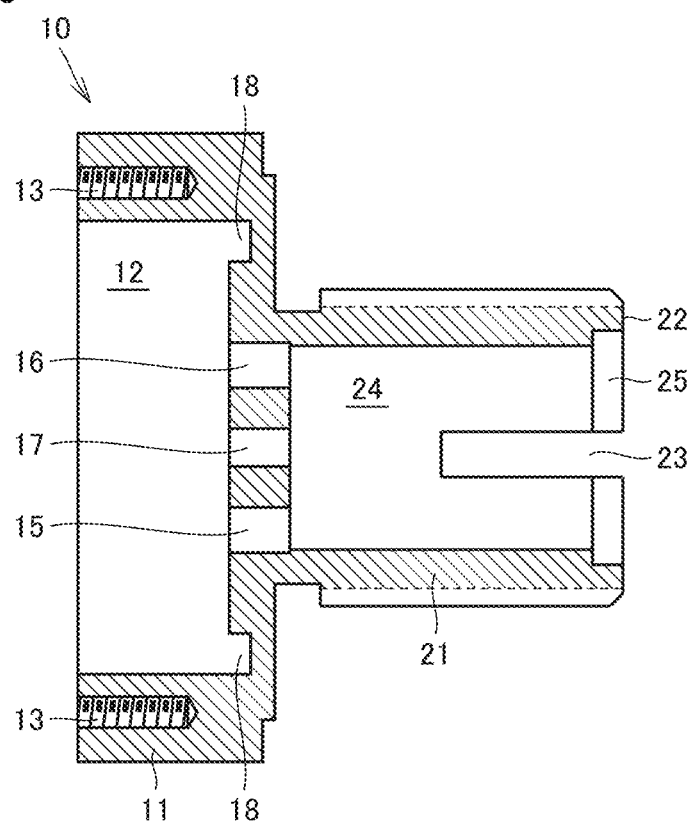
FIG. 5 is a cross-sectional view of the fixing member taken along a line V-V in each of FIGS. 3 and 4.

FIG. 2 is a perspective view of fixing member 10 shown in FIG. 1. FIG. 3 is an outline diagram of fixing member 10 as seen from the direction of an arrow III in FIG. 2. FIG. 4 is an outline diagram of fixing member 10 as seen from the direction of an arrow IV in FIG. 2. FIG. 5 is a cross-sectional view of fixing member 10 taken along a line V-V in each of FIGS. 3 and 4.

As shown in FIGS. 2 to 5, head portion 11 and thread portion 21 of fixing member 10 are formed to be hollow. On the inside of head portion 11, a hollow accommodation space 12 is formed. On the inside of thread portion 21, a hollow accommodation space 24 is formed. Accommodation space 12 has a bottom surface provided with: an annular groove 18 that is formed of an annular-shaped recess on the bottom surface; and a recess portion 14 formed of an approximately rectangular-shaped recess on the bottom surface. Head portion 11 is also provided with a plurality of bottomed screw holes 13. Each of screw holes 13 is formed in the vicinity of a corresponding one of vertices of the regular hexagon seen in a plan view of head portion 11. The number of screw holes 13 is the same as the number of bolts 80 shown in FIG. 1. Bolts 80 are fastened to their respective screw holes 13, so that fixing member 10 and cover member 60 are integrated with each other.

A wall portion separating accommodation space 12 and accommodation space 24 from each other is provided with three through holes that penetrate through the wall portion in its thickness direction. These through holes allow communication between accommodation space 12 and accommodation space 24. These through holes include: wiring line through holes 15 and 16 through which wiring lines (described later) pass; and a fixing hole 17 for fixing a holding member (described later).

Fixing hole 17 is provided at the center position of fixing member 10 shown in FIGS. 3 and 4. Wiring line through holes 15 and 16 each are provided at the position equally distant from the center of fixing member 10. Wiring line through holes 15 and 16 and fixing hole 17 are arranged side by side on a straight line, as shown in FIGS. 3 and 4. The above-described arrangement of wiring line through holes 15 and 16 and fixing hole 17 is merely by way of example, and the positions of these holes are changed depending on the thickness and/or the eccentricity of each element.

Thread portion 21 is provided with a diameter increasing space 25 formed as a hollow space. Diameter increasing space 25 is opened at distal end face 22 of thread portion 21. Accommodation space 24 is opened at distal end face 22 of thread portion 21 through diameter increasing space 25. Diameter increasing space 25 is in communication with accommodation space 24. As shown in FIGS. 4 and 5, diameter increasing space 25 is larger in inner diameter than accommodation space 24. The groove formed in thread portion 21 so as to constitute oil infiltrating space 23 is divided into two portions by accommodation space 24 and diameter increasing space 25, as shown in FIG. 4.

Figure 6:
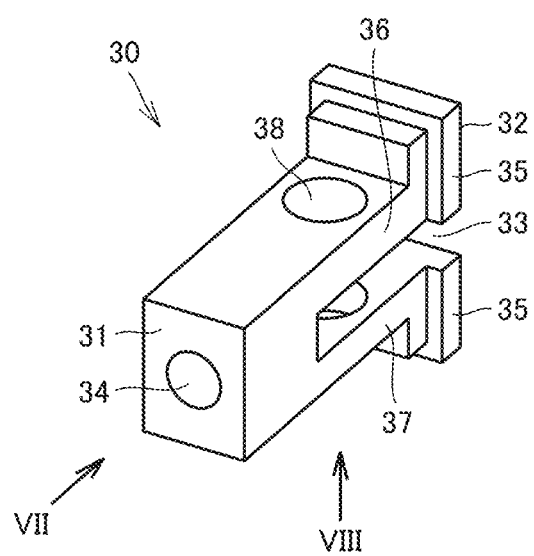
FIG. 6 is a perspective view of a holding member.
Figure 7:
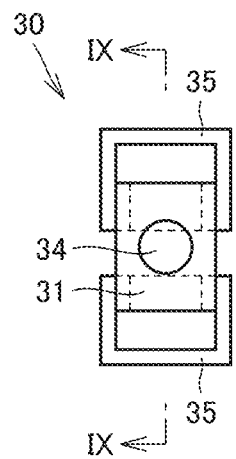
FIG. 7 is an outline diagram of the holding member as seen from the direction of an arrow VII in FIG. 6.
Figure 8:
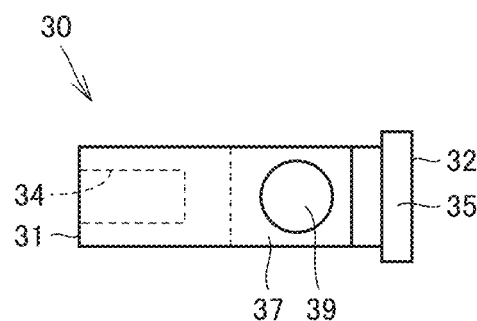
FIG. 8 is an outline diagram of the holding member as seen from the direction of an arrow VIII in FIG. 6.
Figure 9:
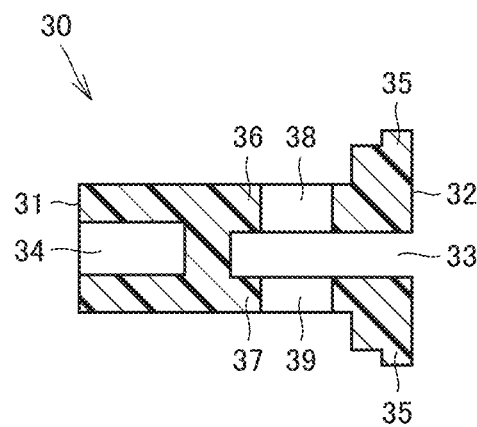
FIG. 9 is a cross-sectional view of the holding member taken along a line IX-IX in FIG. 7.

Accommodation space 24 in fixing member 10 accommodates: a light emitting element configured to emit light; a light receiving element configured to receive light; a substrate on which the light emitting element and the light receiving element are mounted; and a holding member 30 configured to hold the light emitting element, the light receiving element, and the substrate. FIG. 6 is a perspective view of holding member 30. FIG. 7 is an outline diagram of holding member 30 as seen from the direction of an arrow VII in FIG. 6. FIG. 8 is an outline diagram of holding member 30 as seen from the direction of an arrow VIII in FIG. 6. FIG. 9 is a cross-sectional view of holding member 30 taken along a line IX-IX in FIG. 7.

As shown in FIGS. 6 to 9, holding member 30 has a distal end face 31 and a proximal end face 32. Distal end face 31 and proximal end face 32 each have a plane shape. Distal end face 31 and proximal end face 32 are provided in parallel with each other. Distal end face 31 is formed in a rectangular shape. Distal end face 31 has a center portion provided with a bottomed hole 34. An insert nut is inserted into hole 34. Proximal end face 32 may be formed in a disc shape, in which case accommodation space 24 provided in fixing member 10 is formed in a columnar shape.

The length across distal end face 31 is less than the length across proximal end face 32. In holding member 30, proximal end face 32 is greater in diameter than distal end face 31.

Holding member 30 has a diameter increasing portion 35 at proximal end face 32. The shape of the outer circumference of diameter increasing portion 35 is approximately the same as the shape of the inner circumference of diameter increasing space 25 of fixing member 10. On the other hand, the shape of the outer circumference of distal end face 31 is smaller than the shape of the inner circumference of accommodation space 24 of fixing member 10.

Holding member 30 is provided with a groove formed of a partial recess on proximal end face 32. Proximal end face 32 has a shape obtained by dividing a rectangular shape along this groove into two portions. This groove extends in the short side direction of the rectangle corresponding to the shape of the outer edge of proximal end face 32. The groove formed on proximal end face 32 constitutes an oil infiltrating space 33 into which lubricating oil infiltrates. The width of oil infiltrating space 33 in holding member 30 (the dimension across oil infiltrating space 33 in the up-down direction in FIG. 9) is equal to the width of oil infiltrating space 23 in fixing member 10 (the dimension across oil infiltrating space 23 in the up-down direction in FIG. 5).

Holding member 30 in the vicinity of proximal end face 32 is divided by oil infiltrating space 33 into two portions including a light receiving element support portion 36 and a light emitting element support portion 37. Light receiving element support portion 36 is provided with a through hole penetrating through light receiving element support portion 36. This through hole constitutes a light receiving element accommodating hole 38 in which a light receiving element is accommodated. Light emitting element support portion 37 is provided with a through hole penetrating through light emitting element support portion 37. This through hole constitutes a light emitting element accommodating hole 39 in which a light emitting element is accommodated.

Holding member 30 may be a resin molded product. Alternatively, holding member 30 may be made of a metal material such as an aluminum alloy.

Figure 10:
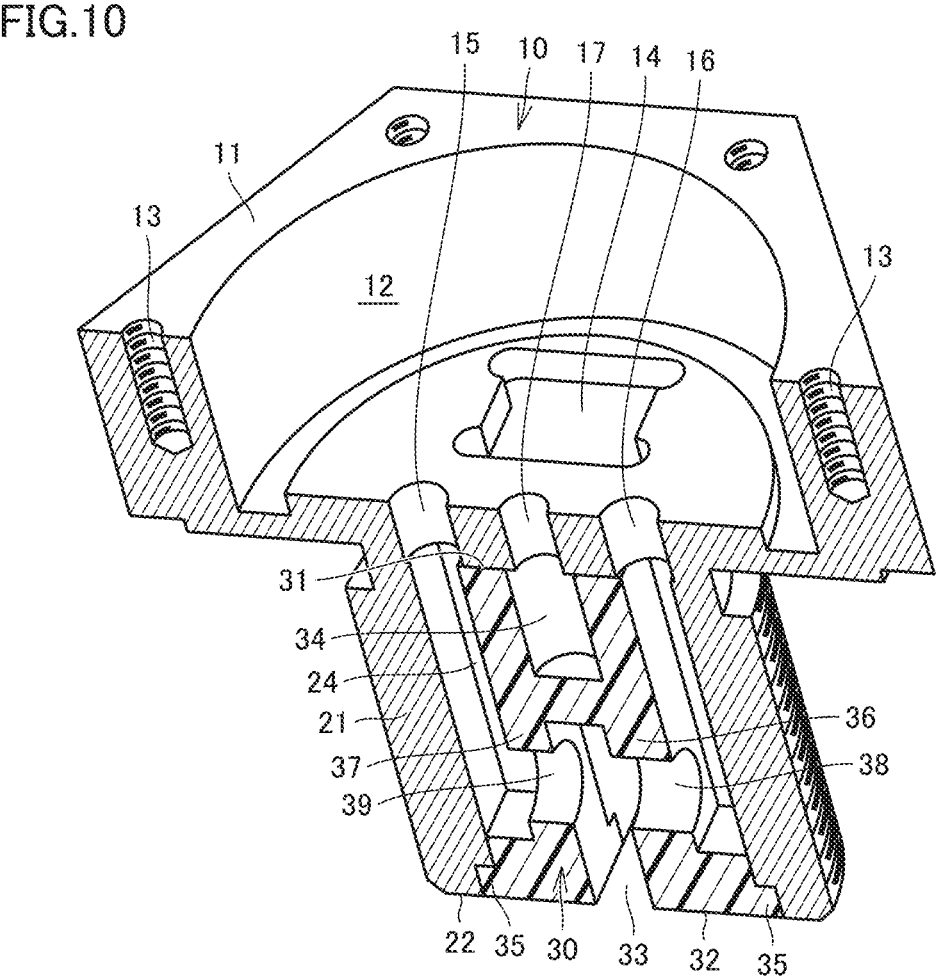
FIG. 10 is a perspective view showing the state where the holding member is installed in the fixing member.
Figure 11:
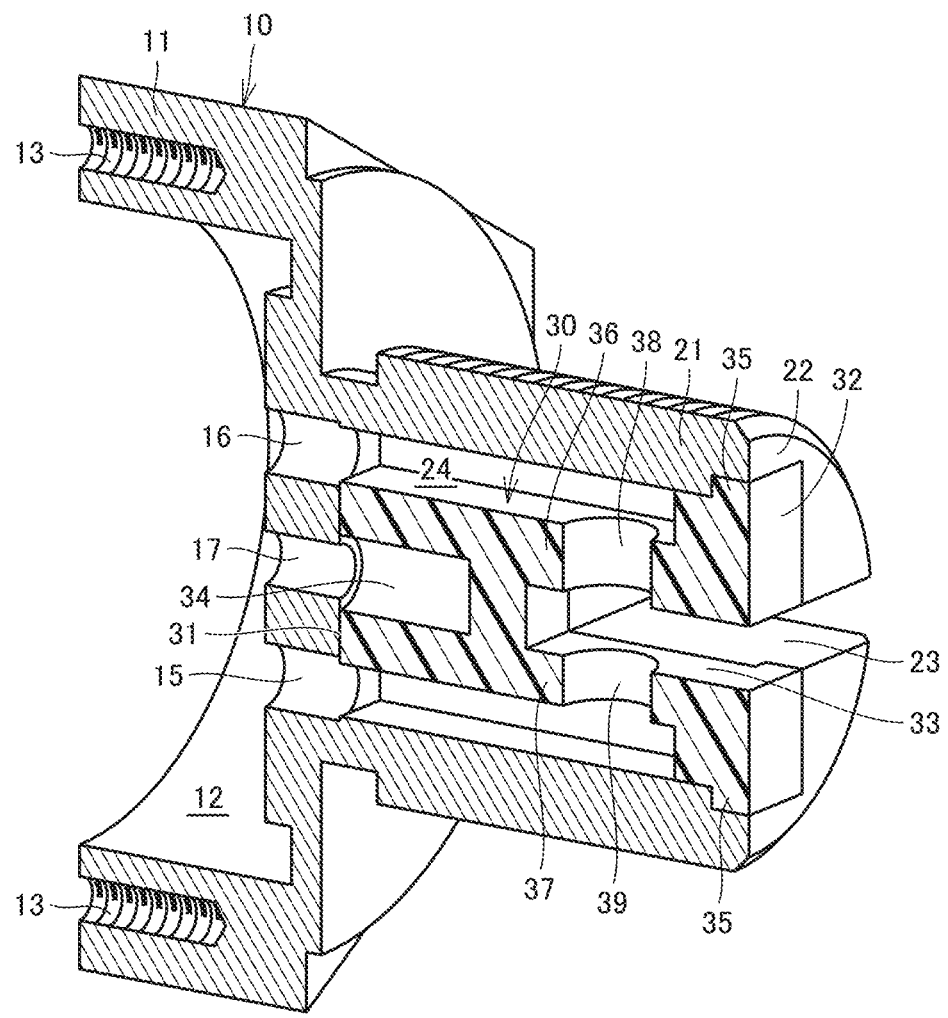
FIG. 11 is a perspective view showing the state where the holding member is installed in the fixing member, which is shown at a different angle.

FIG. 10 is a perspective view showing the state where holding member 30 is installed in fixing member 10. FIG. 11 is a perspective view showing the state where holding member 30 is installed in fixing member 30, which is shown at a different angle. Holding member 30 is shaped such that proximal end face 32 is greater in outer diameter dimension than distal end face 31. Distal end face 31 of holding member 30 is inserted from the distal end face 22 side of fixing member 10 through diameter increasing space 25 into accommodation space 24, so that diameter increasing portion 35 is accommodated inside diameter increasing space 25 and other remaining portion of holding member 30 is accommodated inside accommodation space 24, with the result that the arrangement shown in FIGS. 10 and 11 is implemented.

Since the shape of the outer circumference of diameter increasing portion 35 is almost the same as the shape of the inner circumference of diameter increasing space 25, diameter increasing portion 35 almost engages with diameter increasing space 25, as shown in FIGS. 10 and 11. In the state where holding member 30 is installed in fixing member 10, distal end face 22 of fixing member 10 and proximal end face 32 of holding member 30 are positioned approximately on the same plane. Oil infiltrating space 23 formed in fixing member 10 is identical in width to oil infiltrating space 33 formed in holding member 30. In the state where holding member 30 is installed in fixing member 10, the inner wall surface of oil infiltrating space 23 and the inner wall surface of oil infiltrating space 33 are positioned approximately on the same plane.

The outer circumferential shape in the vicinity of distal end face 31 of holding member 30 is smaller than the inner circumferential shape of accommodation space 24. Accordingly, as shown in FIGS. 10 and 11, in the state where holding member 30 is accommodated inside accommodation space 24, a part of accommodation space 24 still exists as a hollow space. Accommodation space 24 is partitioned by holding member 30 into two hollow spaces. One hollow space is in communication with wiring line through hole 15, and the other hollow space is in communication with wiring line through hole 16. One hollow space is in communication with accommodation space 12 through wiring line through hole 15, and the other hollow space is in communication with accommodation space 12 through wiring line through hole 16.

Hole 34 formed in holding member 30 is in communication with fixing hole 17 of fixing member 10. Hole 34 is in communication with accommodation space 12 through fixing hole 17.

Figure 12:
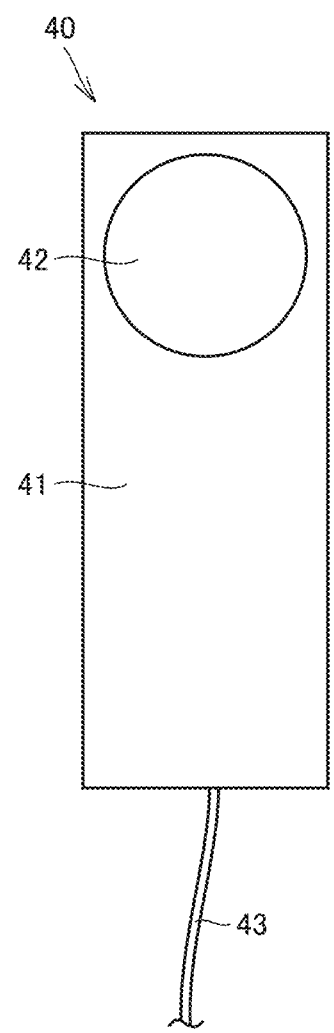
FIG. 12 is a schematic diagram showing the schematic configuration of a light receiving element module.

FIG. 12 is a schematic diagram showing the schematic configuration of a light receiving element module 40. Light receiving element module 40 includes a substrate 41. Substrate 41 has a main surface on which a light receiving element 42 is mounted. Light receiving element 42 serves as an electronic component, for example, as a photodiode, configured to receive the light emitted from light emitting element 52. A wiring line 43 is connected to substrate 41. The amount of light received by light receiving element 42 is output to the outside through wiring line 43.

Figure 13:
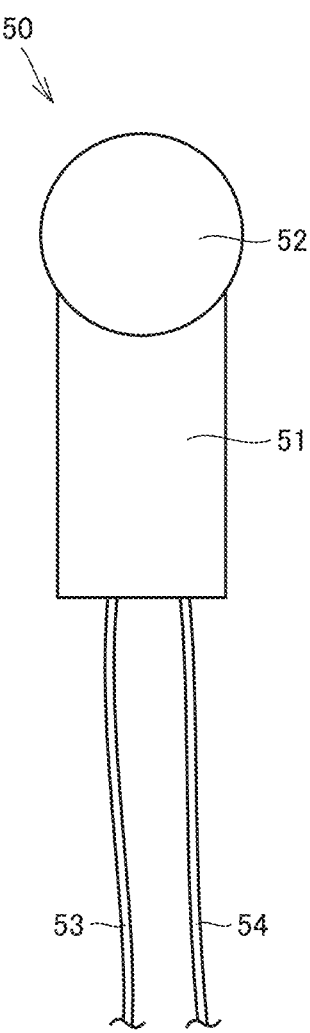
FIG. 13 is a schematic diagram showing the schematic configuration of a light emitting element module.

FIG. 13 is a schematic diagram showing the schematic configuration of a light emitting element module 50. Light emitting element module 50 includes a substrate 51. Substrate 51 has a main surface on which light emitting element 52 is mounted. Light emitting element 52 serves as an electronic component configured to emit monochromatic light, for example. Light emitting element 52 is a red light emitting diode (LED), for example. Wiring lines 53 and 54 are connected to substrate 51. Light emitting element 52 receives a power supply through wiring lines 53 and 54. Also, light emitting element 52 receives an input of a signal for instructing the presence or absence of light emission and the amount of light emission.

Light emitting element 52 may be a white LED configured to emit white light. In this case, light receiving element 42 may be an RGB sensor configured to detect the color of the received light.

Figure 14:
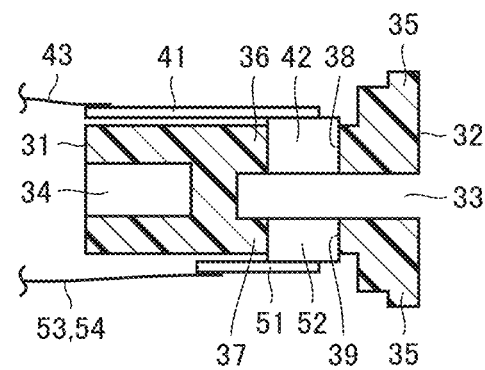
FIG. 14 is a partial cross-sectional view showing the state where the light receiving element module and the light emitting element module are installed in the holding member.

FIG. 14 is a partial cross-sectional view showing the state where light receiving element module 40 and light emitting element module 50 are installed in holding member 30.

Referring to FIGS. 9 and 14, light receiving element 42 is accommodated in light receiving element accommodating hole 38 formed in light receiving element support portion 36 of holding member 30. Light emitting element 52 is accommodated in light emitting element accommodating hole 39 formed in light emitting element support portion 37 of holding member 30. Light receiving element 42 and light emitting element 52 face each other with oil infiltrating space 33 interposed therebetween. Light receiving element 42 and light emitting element 52 are exposed to oil infiltrating space 33. Light receiving element 42 and light emitting element 52 each have oil-tightness (or air-tightness). Accordingly, the lubricating oil inside oil infiltrating space 33 is prevented from infiltrating into light receiving element 42 and light emitting element 52.

Substrate 41 having light receiving element 42 mounted thereon and substrate 51 having light emitting element 52 mounted thereon extend along the outer surface of holding member 30 toward distal end face 31. Wiring line 43 and wiring lines 53 and 54 extend further beyond distal end face 31. In the state where holding member 30 is installed in fixing member 10, wiring line 43 penetrates through wiring line through hole 16 and extends to accommodation space 12. In the state where holding member 30 is installed in fixing member 10, wiring lines 53 and 54 penetrate through wiring line through hole 15 and extend to accommodation space 12.

Figure 15:
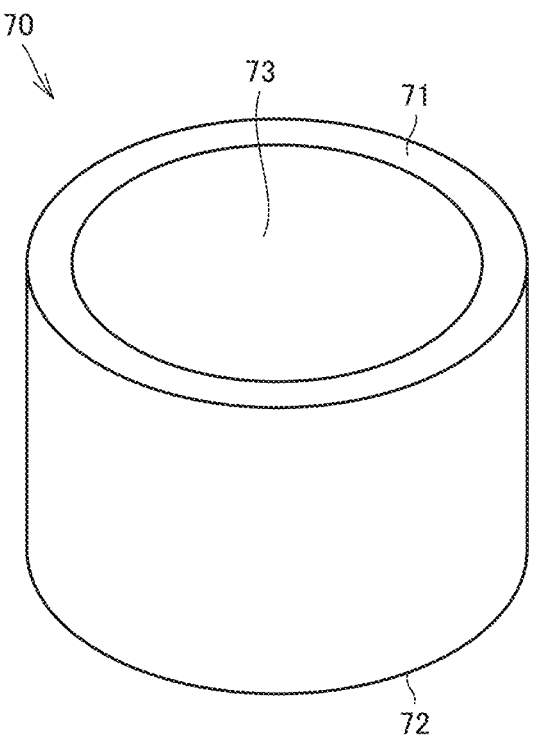
FIG. 15 is a perspective view of a heat insulating member.

FIG. 15 is a perspective view of heat insulating member 70. Heat insulating member 70 is formed in a hollow cylindrical shape. Heat insulating member 70 may be formed in a hollow prism shape. Heat insulating member 70 has one end 71 and the other end 72. A hollow accommodation space 73 is formed inside heat insulating member 70.

Figure 16:
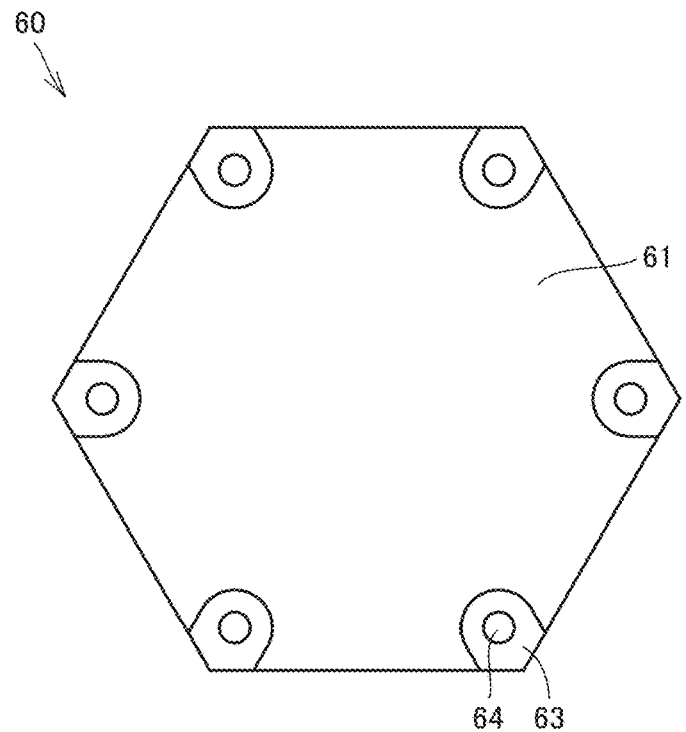
FIG. 16 is a plan view of a cover member.

FIG. 16 is a plan view of cover member 60. In addition, FIG. 16 shows cover member 60 with no bolt 80 (FIG. 1) attached thereto, as seen in a top-down view of FIG. 1. Cover member 60 seen in a plan view has a regular hexagonal outer shape. Cover member 60 has an approximately plate shape, and also includes a first surface 61 and a second surface 62 (not shown in FIG. 16) that is located on the opposite side of first surface 61. Cover member 60 is provided with a plurality of recesses 63 formed of recesses on first surface 61 at vertices of its hexagonal shape. Cover member 60 is also provided with through holes 64 that are identical in number to recesses 63 and that penetrate at their respective positions of recesses 63 through cover member 60 in the thickness direction thereof.

Figure 17:
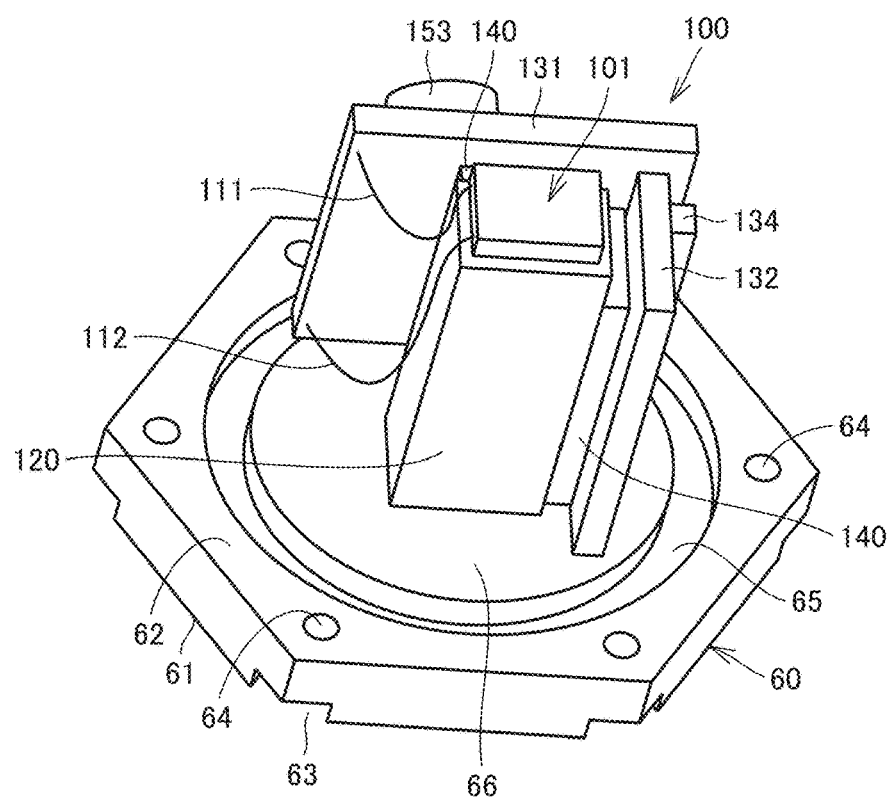
FIG. 17 is a perspective view showing the schematic configuration of a thermoelectric power generation unit.

FIG. 17 is a perspective view showing the schematic configuration of a thermoelectric power generation unit 100. Thermoelectric power generation unit 100 is attached to the second surface 62 side of cover member 60. Second surface 62 is provided with an annular groove 65 formed of an annular recess on second surface 62. On the inner circumferential side of annular groove 65, an island-shaped portion 66 is formed. Thermoelectric power generation unit 100 is fixed to island-shaped portion 66.

Thermoelectric power generation unit 100 mainly includes a thermoelectric power generation module 101, a pillar member 120, and substrates 131, 132. Pillar member 120 is formed in the shape of a quadrangular prism. Pillar member 120 has a proximal end that is fixed to cover member 60. Thermoelectric power generation module 101 is attached to a distal end of pillar member 120. Pillar member 120 may be formed integrally with cover member 60. Alternatively, pillar member 120 may be fixed to cover member 60 using a thermally conducting adhesive. Pillar member 120 is thermally integrated with cover member 60. Pillar member 120 is formed of a material with high thermal conductivity such as a metal material. Pillar member 120 may be formed of a material with high heat dissipation performance such as an aluminum alloy, for example. Thermoelectric power generation module 101 may be attached to the proximal end of pillar member 120 that is on the opposite side of the distal end shown in FIG. 17, or may be interposed between two halves obtained by dividing pillar member 120.

Each of substrates 131 and 132 is attached to the side surface of pillar member 120 with an attachment member 140 interposed therebetween. Substrates 131 and 132 may be attached to cover member 60. Attachment member 140 is a sheet-shaped member having adhesiveness, for example, and may be affixed to the side surface of pillar member 120 and also to substrates 131 and 132. An electronic component 133 is mounted on substrate 131. An electronic component 134 is mounted on substrate 132. The electronic components mounted on substrates 131 and 132 may constitute a power supply circuit. The electronic components mounted on substrates 131 and 132 may constitute a wireless communication circuit configured to wirelessly transmit the detection result from light receiving element 42.

Thermoelectric power generation module 101 and substrate 131 are electrically connected through wiring lines 111 and 112. Substrate 131 and substrate 132 are electrically connected to each other.

Figure 18:
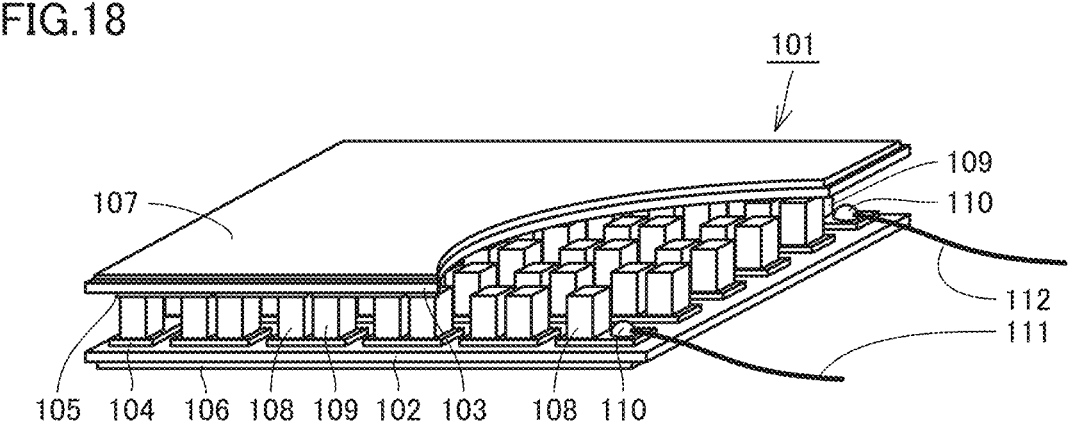
FIG. 18 is a perspective view showing the schematic configuration of a thermoelectric power generation module.

FIG. 18 is a perspective view showing the schematic configuration of thermoelectric power generation module 101. Thermoelectric power generation module 101 is configured such that a p-type thermoelectric conversion element 108 and an n-type thermoelectric conversion element 109 are joined so as to be electrically connected in series in an alternate manner between a heat dissipation-side substrate 102 and a cooling-side substrate 103.

Heat dissipation-side substrate 102 and cooling-side substrate 103 each are made, for example, of $Al_2O_3$ (aluminum oxide), AlN (aluminum nitride), SiC (silicon carbide), $Si_3N_4$ (silicon nitride), metal having an outer circumferential surface on which an insulation layer is formed, and the like.

A plurality of heat dissipation-side electrodes 104 are formed by plating or the like on an element mount surface (upper surface) of heat dissipation-side substrate 102. A pair of p-type thermoelectric conversion element 108 and n-type thermoelectric conversion element 109 each made of a BiTe-based material is mounted on each of independent heat dissipation-side electrodes 104. Thereby, p-type thermoelectric conversion element 108 and n-type thermoelectric conversion element 109 are electrically connected to heat dissipation-side electrode 104.

Similarly, a plurality of cooling-side electrodes 105 are formed by plating or the like also on the element mount surface (lower surface) of cooling-side substrate 103. A pair of p-type thermoelectric conversion element 108 and n-type thermoelectric conversion element 109 each made of a BiTe-based material is mounted on each of independent cooling-side electrodes 105. Thereby, p-type thermoelectric conversion element 108 and n-type thermoelectric conversion element 109 are electrically connected to cooling-side electrode 105.

Heat dissipation-side electrode 104 is displaced relative to cooling-side electrode 105. Consequently, p-type thermoelectric conversion elements 108 and n-type thermoelectric conversion elements 109, which are joined between heat dissipation-side electrode 104 and cooling-side electrode 105, are electrically connected alternately in series.

In addition, a metallization layer 106 for allowing junction with a heat dissipating object is formed on the back surface of the element mount surface (lower surface) of heat dissipation-side substrate 102. Metallization layers 107 for allowing junction with a cooled object are formed also on the back surface of the element mount surface (upper surface) of cooling-side substrate 103.

Furthermore, wiring lines 111 and 112, which are used for supplying electric power to thermoelectric power generation module 101, are attached onto the upper surface of heat dissipation-side substrate 102. Specifically, wiring line 111 is attached with solder 110 onto heat dissipation-side electrode 104 on which only one p-type thermoelectric conversion element 108 is mounted. Also, wiring line 112 is attached with solder 110 onto heat dissipation-side electrode 104 on which only one n-type thermoelectric conversion element 109 is mounted. Thereby, wiring lines 111 and 112 are electrically connected to heat dissipation-side electrode 104.

Thermoelectric power generation module 101 converts the temperature difference between heat dissipation-side substrate 102 and cooling-side substrate 103 into electric power. Thermoelectric power generation module 101 supplies the generated electric power to light emitting element 52, light receiving element 42, and the electronic circuits mounted on substrates 131 and 132.

Figure 19:
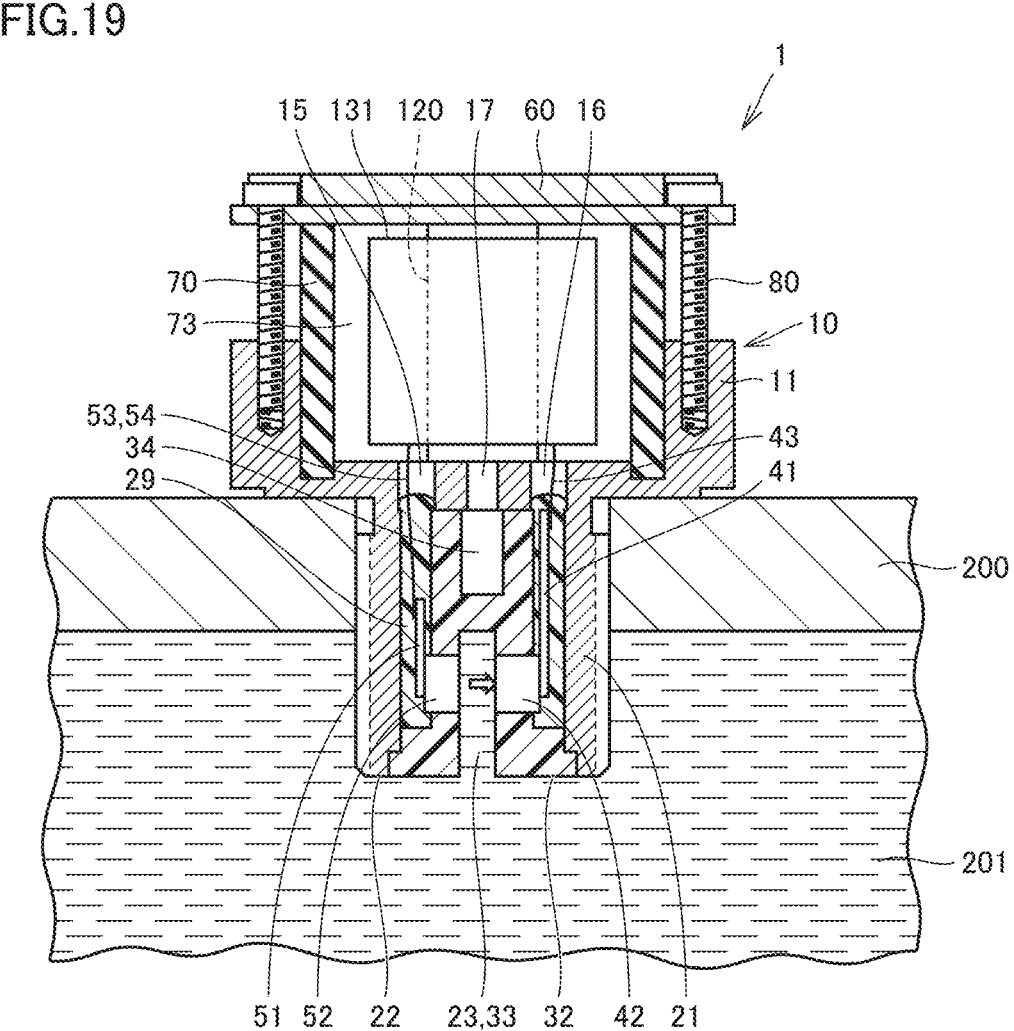
FIG. 19 is a cross-sectional view showing the state where the optical sensor according to the first embodiment is installed in a machine.

FIG. 19 is a cross-sectional view showing the state where optical sensor 1 according to the first embodiment is installed in a machine. The machine in which optical sensor 1 is installed includes a housing 200. Optical sensor 1 is fixed to housing 200 by fastening thread portion 21 of fixing member 10 to housing 200. A tool (not shown) is used to grasp hexagonal prism-shaped head portion 11 to rotate head portion 11 with respect to the screw hole provided in housing 200, thereby fastening thread portion 21 to housing 200. Housing 200 has an internal space containing lubricating oil 201. In order to prevent lubricating oil 201 from leaking to the outside, a sealing member (not shown) is provided between the outer surface of housing 200 and head portion 11.

Substrates 41 and 51 are accommodated in accommodation space 24 existing as a hollow space in the state where holding member 30 is installed in fixing member 10, as shown in FIGS. 10 and 11. Accommodation space 24 contains sealing resin 29. After holding member 30 having light receiving element module 40 and light emitting element module 50 installed therein is accommodated in accommodation space 24, a liquid resin material is introduced through wiring line through holes 15 and 16 into accommodation space 24 and hardened, thereby providing sealing resin 29.

Sealing resin 29 covers the entire circumference of each of substrates 41 and 51. Substrates 41 and 51 accommodated in accommodation space 24 and parts of wiring lines 43, 53 and 54 are sealed by sealing resin 29. Thereby, lubricating oil 201 is prevented from reaching substrates 41 and 51. As described above, light receiving element 42 and light emitting element 52 each have oil-tightness, thereby suppressing an adverse effect of lubricating oil 201 from being exerted upon each of electronic components constituting light receiving element module 40 and light emitting element module 50.

An insert nut (not shown) is embedded in hole 34 provided in holding member 30. Fixing hole 17 in fixing member 10 is a bolt hole. Thus, a bolt (not shown) is rotated so as to be screwed into the insert nut embedded in hole 34, thereby improving the assembly strength for holding member 30 and fixing member 10.

Accommodation space 12 (FIGS. 2 and 5) provided inside head portion 11 of fixing member 10 accommodates: a part of heat insulating member 70; thermoelectric power generation module 101 that is not shown in FIG. 19; a part of pillar member 120; a part of substrate 131; and a part of substrate 132 that is not shown in FIG. 19. Fixing member 10 and cover member 60 are disposed at a distance from each other in the up-down direction in FIG. 19. Also, the bottom surface of accommodation space 12 and second surface 62 (FIG. 17) face each other. The bottom surface of accommodation space 12 and second surface 62 are arranged side by side approximately in parallel with each other.

Heat insulating member 70 and thermoelectric power generation unit 100 are disposed between fixing member 10 and cover member 60. Pillar member 120 and substrates 131, 132 are disposed between fixing member 10 and cover member 60. Heat insulating member 70 thermally separates fixing member 10 and cover member 60 from each other.

One end 71 (FIG. 15) of heat insulating member 70 is accommodated in annular groove 65 (FIG. 17) formed on second surface 62 of cover member 60. The other end 72 (FIG. 15) of heat insulating member 70 is accommodated in annular groove 18 (FIGS. 2 and 5) formed on the bottom surface of accommodation space 12. Heat insulating member 70, which is interposed between cover member 60 and fixing member 10, is not fixed to cover member 60 and also not fixed to fixing member 10. One end 71 of heat insulating member 70 is in contact with cover member 60 without being fixed to cover member 60. The other end 72 of heat insulating member 70 is in contact with fixing member 10 without being fixed to fixing member 10.

An O ring (not shown) is disposed between one end 71 of heat insulating member 70 and cover member 60, and between the other end 72 of heat insulating member 70 and fixing member 10. One end 71 of heat insulating member 70 is in contact with cover member 60 with the O ring interposed therebetween. The other end 72 of heat insulating member 70 is in contact with fixing member 10 with the O ring interposed therebetween. This O ring is provided for sealing hollow accommodation space 73 provided inside heat insulating member 70. Thermoelectric power generation unit 100 is accommodated in accommodation space 73.

Heat dissipation-side substrate 102 (FIG. 18) of thermoelectric power generation module 101 is disposed inside recess portion 14 (FIGS. 2 and 5) formed on the bottom surface of accommodation space 12. Heat dissipation-side substrate 102 is in contact with the bottom surface of accommodation space 12 with the member such as a carbon sheet interposed therebetween, which is excellent in thermal conductivity and deformed in the thickness direction. Heat dissipation-side substrate 102 is in contact with fixing member 10. Heat dissipation-side electrode 104 is in thermal contact with fixing member 10 with heat dissipation-side substrate 102 interposed therebetween.

Cooling-side substrate 103 (FIG. 18) of thermoelectric power generation module 101 is in contact with pillar member 120. Cooling-side substrate 103 is in thermal contact with cover member 60 with pillar member 120 interposed therebetween. Cooling-side electrode 105 is in thermal contact with cover member 60 with pillar member 120 and cooling-side substrate 103 interposed therebetween. Pillar member 120 is in contact with cover member 60 and cooling-side substrate 103 of thermoelectric power generation module 101.

Fixing member 10 is heated by heat transfer from lubricating oil 201. Cover member 60 is exposed to atmospheric air. In thermoelectric power generation unit 100, fixing member 10 constitutes a higher-temperature side heat conductor. Cover member 60 constitutes a lower-temperature side heat conductor. Heat dissipation-side electrode 104 constitutes a higher-temperature side electrode that is in thermal contact with the higher-temperature side heat conductor. Cooling-side electrode 105 constitutes a lower-temperature side electrode that is in thermal contact with the lower-temperature side heat conductor. Pillar member 120 constitutes a heat conducting member that is in contact with the lower-temperature side heat conductor and thermoelectric power generation module 101. Thermoelectric power generation module 101 is provided on the higher-temperature side with respect to pillar member 120.

Bolt 80 penetrates through the through hole 64 (FIG. 16) formed in cover member 60 so as to be fastened to screw hole 13 (FIGS. 3 and 5) formed in head portion 11 of fixing member 10. Bolt 80 is made of a material different from the material of heat insulating member 70. Fixing member 10 and cover member 60 are integrally fastened to each other by bolt 80 with heat insulating member 70 interposed therebetween.

Bolt 80 has a head portion that is in contact with cover member 60. Bolt 80 has a thread portion that is in contact with head portion 11 of fixing member 10. Bolt 80 is in contact with both cover member 60 and fixing member 10. Bolt 80 does not engage with heat insulating member 70 but directly engages with fixing member 10 and cover member 60 to integrally fasten fixing member 10 and cover member 60. In thermoelectric power generation unit 100, bolt 80 constitutes an integrating member for integrating the higher-temperature side heat conductor and the lower-temperature side heat conductor with each other.

The direction in which bolt 80 extends (the up-down direction in FIG. 19) corresponds to the direction in which pillar member 120 of thermoelectric power generation unit 100 extends. Heat dissipation-side electrode 104 and cooling-side electrode 105 of thermoelectric power generation module 101 are arranged side by side so as to be spaced apart from each other in the up-down direction in FIG. 19. In this case, the direction in which bolt 80 extends corresponds to the direction in which heat dissipation-side electrode 104 and cooling-side electrode 105 are arranged side by side.

Bolt 80 extends in the thickness direction of cover member 60 that has an approximately plate-shaped outer shape, and also extends in the direction that is orthogonal to the bottom surface of accommodation space 12 and second surface 62 that are arranged in parallel with each other. Heat insulating member 70 has a cylindrical shape, and bolt 80 extends in the axial direction of heat insulating member 70.

Bolt 80 may be formed of a metal material such as an aluminum alloy. Alternatively, bolt 80 may be formed of a resin material, for example, a material having electrical insulation such as engineering plastic.

Light emitting element 52 and light receiving element 42 face each other with oil infiltrating space 33 interposed therebetween. Oil infiltrating space 33 formed between light receiving element support portion 36 and light emitting element support portion 37 in holding member 30 is disposed on an optical path extending from light emitting element 52 to light receiving element 42. Lubricating oil 201 infiltrates into oil infiltrating spaces 23 and 33. Light emitting element 52 and light receiving element 42 are exposed to lubricating oil 201.

The optical path extending from light emitting element 52 to light receiving element 42 passes through oil infiltrating space 33 as a space into which lubricating oil 201 infiltrates. The outlined arrow shown in FIG. 19 shows the traveling path of the light emitted from light emitting element 52, traveling through oil infiltrating space 33 and received by light receiving element 42.

Light emitting element 52 receives supply of electric power from thermoelectric power generation module 101 and emits monochromatic light. The light emitted from light emitting element 52 travels through lubricating oil 201 inside oil infiltrating space 33, and then reaches light receiving element 42. Light receiving element 42 receives the light having reached light receiving element 42. Light receiving element 42 outputs the amount of received light as an electrical signal. In the electronic circuits formed on substrates 131 and 132, or in the external apparatus, the amount of foreign substances such as wear powder contained in lubricating oil 201 is calculated based on the amount of light received by light receiving element 42. Based on the data of the amount of foreign substances, deterioration in lubricating oil 201 is monitored, so that malfunctions occurring in a work vehicle or a mechanical apparatus can be detected.

The functions and effects of the present embodiment will then be described.

As shown in FIG. 19, optical sensor 1 in the present embodiment includes light emitting element 52 configured to emit light, and light receiving element 42 configured to receive the light emitted from light emitting element 52. The optical path extending from light emitting element 52 to light receiving element 42 extends through oil infiltrating space 33 as a space into which oil infiltrates. Optical sensor 1 also includes: substrate 51 on which light emitting element 52 is mounted; substrate 41 on which light receiving element 42 is mounted; fixing member 10 provided with accommodation space 24 in which substrates 41 and 51 are accommodated; and sealing resin 29 contained in accommodation space 24 and sealing substrates 41 and 51.

Fixing member 10 constitutes an accommodation member in which substrates 41 and 51 are accommodated.

Sealing resin 29 is contained in accommodation space 24 in which substrates 41 and 51 are accommodated to seal substrates 41 and 51. Accordingly, substrate 51 on which light emitting element 52 is mounted and substrate 41 on which light receiving element 42 is mounted can be reliably supported.

Also, as shown in FIG. 19, light emitting element 52 and light receiving element 42 face each other with oil infiltrating space 33 interposed therebetween. In this way, it becomes possible to suppress that other members interfere with the optical path extending from light emitting element 52 to light receiving element 42.

Furthermore, light emitting element 52 and light receiving element 42 each have oil-tightness. In this way, as shown in FIG. 19, light emitting element 52 and light receiving element 42 can be disposed so as to be exposed to oil infiltrating space 33, with the result that light emitting element 52 and light receiving element 42 can be disposed so as to be exposed to lubricating oil 201. Accordingly, it becomes possible to more reliably suppress that other members interfere with the optical path extending from light emitting element 52 to light receiving element 42.

As shown in FIGS. 17 and 18, optical sensor 1 further includes thermoelectric power generation module 101 configured to supply electric power to light emitting element 52 and light receiving element 42. When the temperature difference between the oil temperature and the atmospheric air temperature around optical sensor 1 is converted by thermoelectric power generation module 101 into electric power, this electric power can be supplied to light emitting element 52 and light receiving element 42 without requiring supply of electric power from the outside.

Second Embodiment

Figure 20:
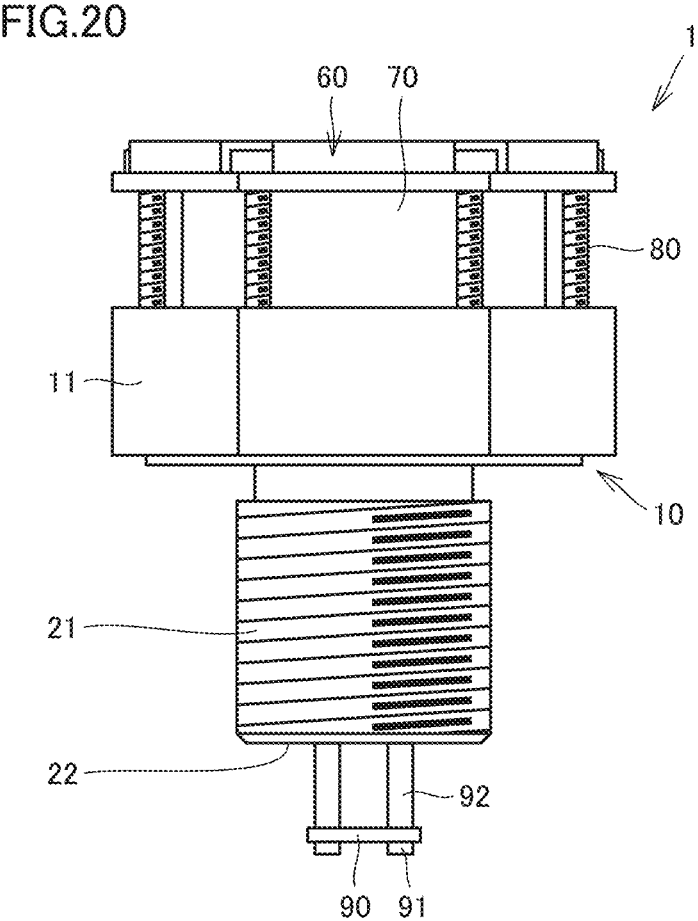
FIG. 20 is a front view of an optical sensor according to the second embodiment.

FIG. 20 is a front view of an optical sensor 1 according to the second embodiment. In contrast to the first embodiment, in optical sensor 1 in the second embodiment, an oil infiltrating space is not provided in thread portion 21 of fixing member 10. Optical sensor 1 in the second embodiment includes a reflective member 90, as shown in FIG. 20. Reflective member 90 is disposed at a distance from distal end face 22 of thread portion 21 and arranged approximately in parallel with distal end face 22. Reflective member 90 is fixed to thread portion 21 with a bolt 91.

A plurality of hollow cylindrical-shaped spacers 92 are disposed between distal end face 22 and reflective member 90. Each bolt 91 penetrates through a corresponding one of spacers 92, and is fastened to thread portion 21. Spacer 92 has a function to specify the distance between distal end face 22 of thread portion 21 and reflective member 90.

Figure 21:
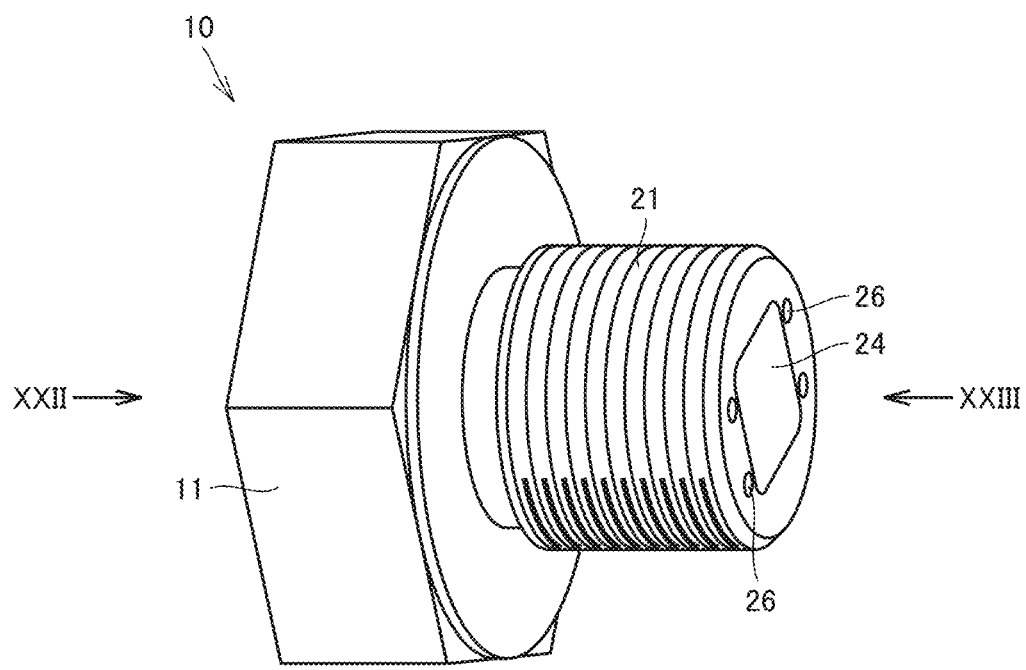
FIG. 21 is a perspective view of a fixing member shown in FIG. 20.
Figure 22:
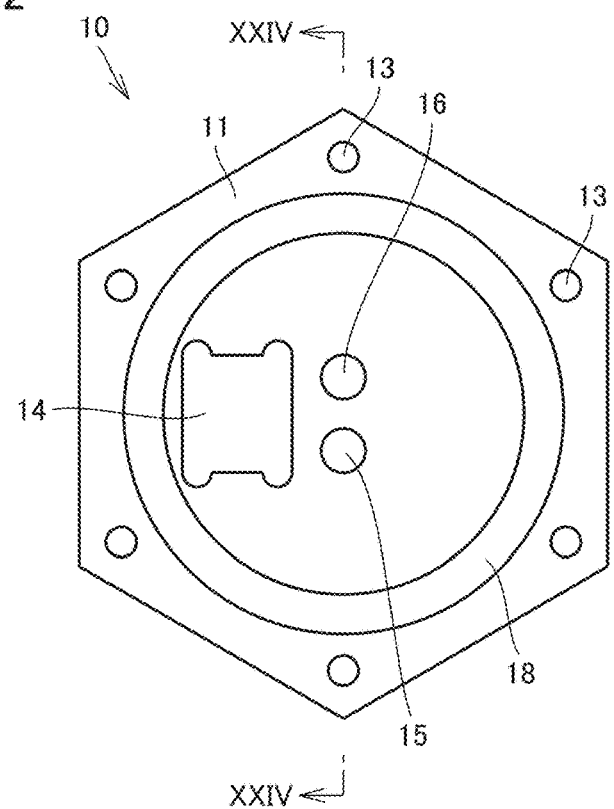
FIG. 22 is an outline diagram of the fixing member as seen from the direction of an arrow XXII in FIG. 21.
Figure 23:
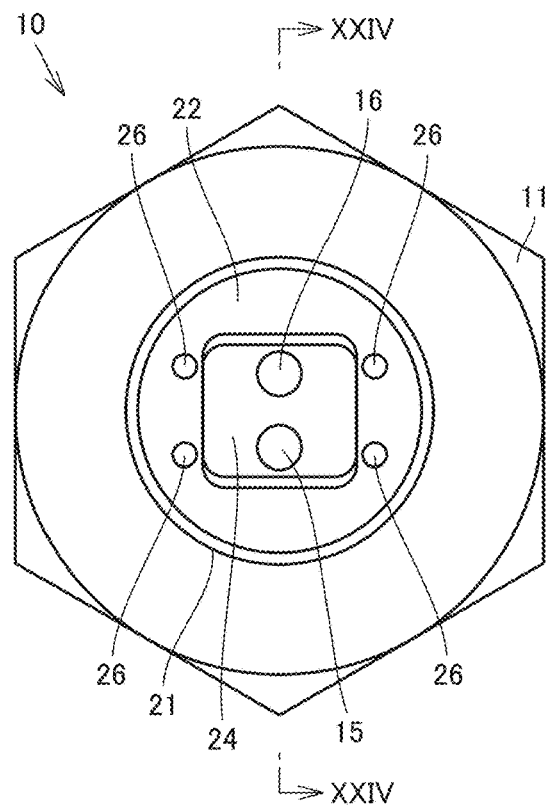
FIG. 23 is an outline diagram of the fixing member as seen from the direction of an arrow XXIII in FIG. 21.
Figure 24:
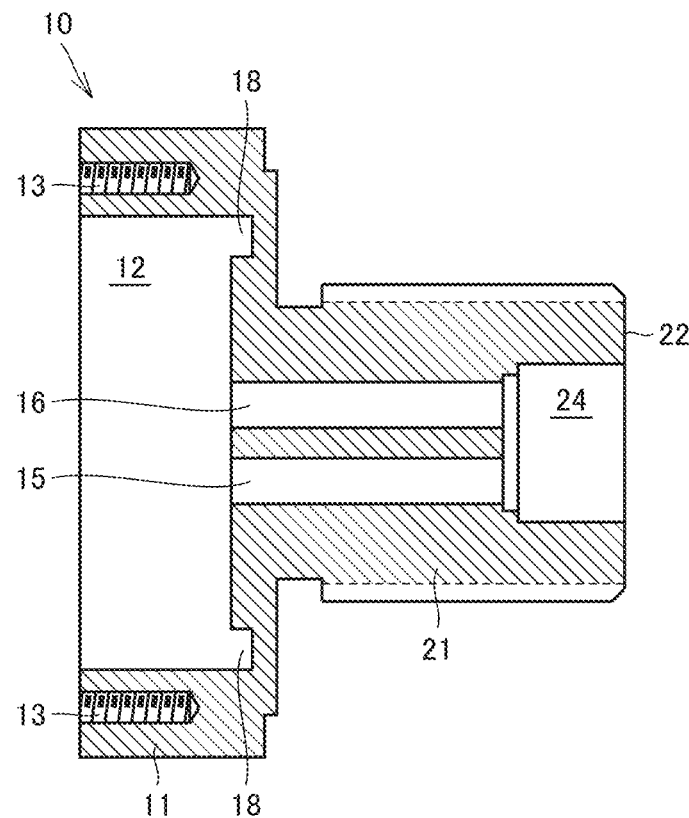
FIG. 24 is a cross-sectional view of the fixing member taken along a line XXIV-XXIV in each of FIGS. 22 and 23.

FIG. 21 is a perspective view of fixing member 10 shown in FIG. 20. FIG. 22 is an outline diagram of fixing member 10 as seen from the direction of an arrow XXII in FIG. 21. FIG. 23 is an outline diagram of fixing member 10 as seen from the direction of an arrow XXIII in FIG. 21. FIG. 24 is a cross-sectional view of fixing member 10 taken along a line XXIV-XXIV in each of FIGS. 22 and 23.

As with fixing member 10 in the first embodiment, a hollow accommodation space 24 is provided inside thread portion 21 of fixing member 10 in the second embodiment. Referring to FIGS. 5 and 24, accommodation space 24 in the second embodiment is provided only in a part in the vicinity of distal end face 22 of thread portion 21, and thus, significantly reduced in volume as compared with accommodation space 24 in the first embodiment.

Fixing member 10 is provided with two wiring line through holes 15 and 16 that allow communication between accommodation space 12 and accommodation space 24. Wiring line through holes 15 and 16 are opened at the bottom surface of accommodation space 12, and also opened at the bottom surface of accommodation space 24. The fixing hole shown in the first embodiment and allowing communication between accommodation space 12 and accommodation space 24 is not formed in fixing member 10 in the second embodiment. Since accommodation space 24 is provided only in the vicinity of distal end face 22 of thread portion 21, wiring line through holes 15 and 16 in the second embodiment are longer than wiring line through holes 15 and 16 in the first embodiment shown in FIG. 5.

As shown in FIG. 23, a plurality of screw holes 26 are formed in distal end face 22 of thread portion 21. Screw holes 26 are formed around accommodation space 24. Accommodation space 24 shown in FIG. 23 has an approximately rectangular shape. Screw holes 26 are provided along two sides of the rectangular shape that face each other. Two screw holes 26 are provided along the first side of the rectangle and the other two screw holes 26 are provided along the second side facing the first side.

Figure 25:
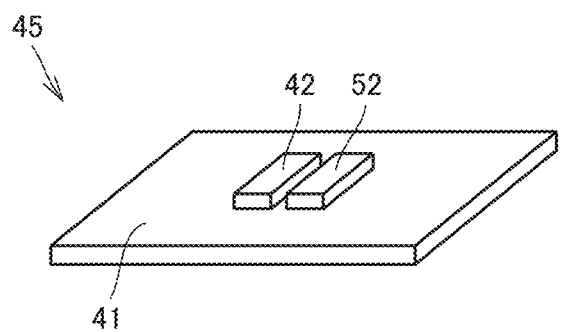
FIG. 25 is a perspective view showing the schematic configuration of a light receiving/light emitting element module.

FIG. 25 is a perspective view showing the schematic configuration of a light receiving/light emitting element module 45. Both light receiving element 42 and light emitting element 52 are mounted on the main surface of one substrate 41, to thereby constitute light receiving/light emitting element module 45.

Figure 26:
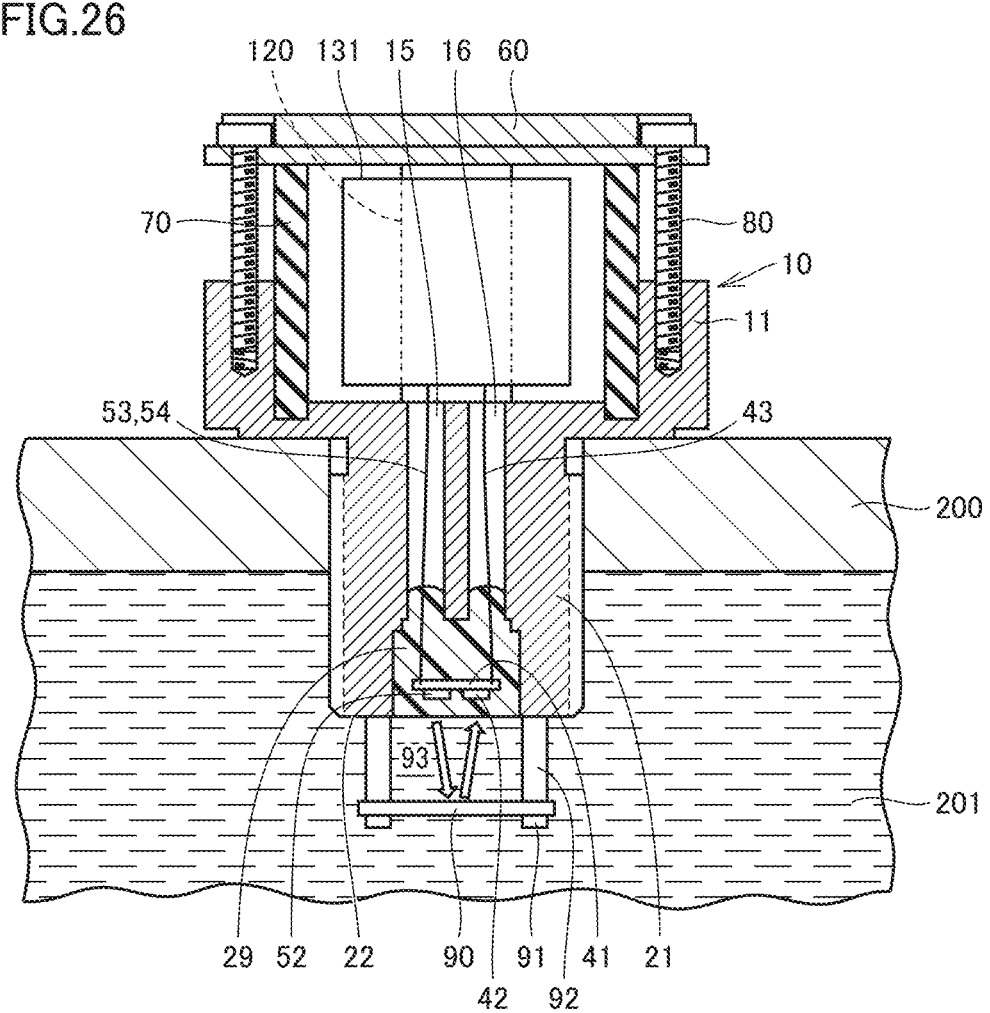
FIG. 26 is a cross-sectional view showing the state where the optical sensor according to the second embodiment is installed in the machine.

FIG. 26 is a cross-sectional view showing the state where optical sensor 1 according to the second embodiment is installed in the machine. Light receiving/light emitting element module 45 is accommodated in accommodation space 24 of fixing member 10. Sealing resin 29 is contained in accommodation space 24. After light receiving/light emitting element module 45 is accommodated in accommodation space 24, a liquid resin material is introduced into accommodation space 24 and hardened, thereby providing sealing resin 29.

Light emitting element 52 and light receiving element 42 are arranged adjacent to each other on the same substrate 41. Oil infiltrating space 93 is formed between distal end face 22 of fixing member 10 and reflective member 90. Light emitting element 52 and reflective member 90 face each other with oil infiltrating space 93 interposed therebetween. Light receiving element 42 and reflective member 90 face each other with oil infiltrating space 93 interposed therebetween. Reflective member 90 reflects the light emitted from light emitting element 52. Light receiving element 42 receives the light reflected by reflective member 90. The outlined arrow shown in FIG. 26 indicates the traveling path of the light emitted from light emitting element 52, passing through oil infiltrating space 93, reflected by reflective member 90, passing through oil infiltrating space 93, and then, received by light receiving element 42. Oil infiltrating space 93 is disposed on the optical path extending from light emitting element 52 to light receiving element 42. Lubricating oil 201 infiltrates into oil infiltrating space 93. The optical path extending from light emitting element 52 through reflective member 90 to light receiving element 42 extends through oil infiltrating space 93 as a space into which lubricating oil 201 infiltrates.

Light emitting element 52 receives supply of electric power from thermoelectric power generation module 101 and emits monochromatic light. The light emitted from light emitting element 52 travels through lubricating oil 201 inside oil infiltrating space 93, and reaches light receiving element 42. Light receiving element 42 receives the light having reached light receiving element 42. Light receiving element 42 outputs the amount of the received light as an electrical signal. In the electronic circuits formed on substrates 131 and 132, or in the external apparatus, the amount of foreign substances such as wear powder contained in lubricating oil 201 is calculated based on the amount of light received by light receiving element 42. Based on the data of the amount of foreign substances, deterioration in lubricating oil 201 is monitored, so that malfunctions occurring in a work vehicle or a mechanical apparatus can be detected.

Optical sensor 1 in the second embodiment as described above further includes reflective member 90 configured to reflect the light emitted from light emitting element 52, as shown in FIGS. 20 and 26. Light receiving element 42 receives the light reflected by reflective member 90. As the light emitted from light emitting element 52 is reflected by reflective member 90, light receiving element 42 can reliably receive the light that has traveled through oil infiltrating space 93 and been reflected by reflective member 90.

Also as shown in FIG. 26, light emitting element 52 and reflective member 90 face each other with oil infiltrating space 93 interposed therebetween. Light receiving element 42 and reflective member 90 face each other with oil infiltrating space 93 interposed therebetween. In this way, the light emitted from light emitting element 52 can be reliably reflected by reflective member 90, and also, the light reflected by reflective member 90 can be reliably received by light receiving element 42.

Third Embodiment

Figure 27:
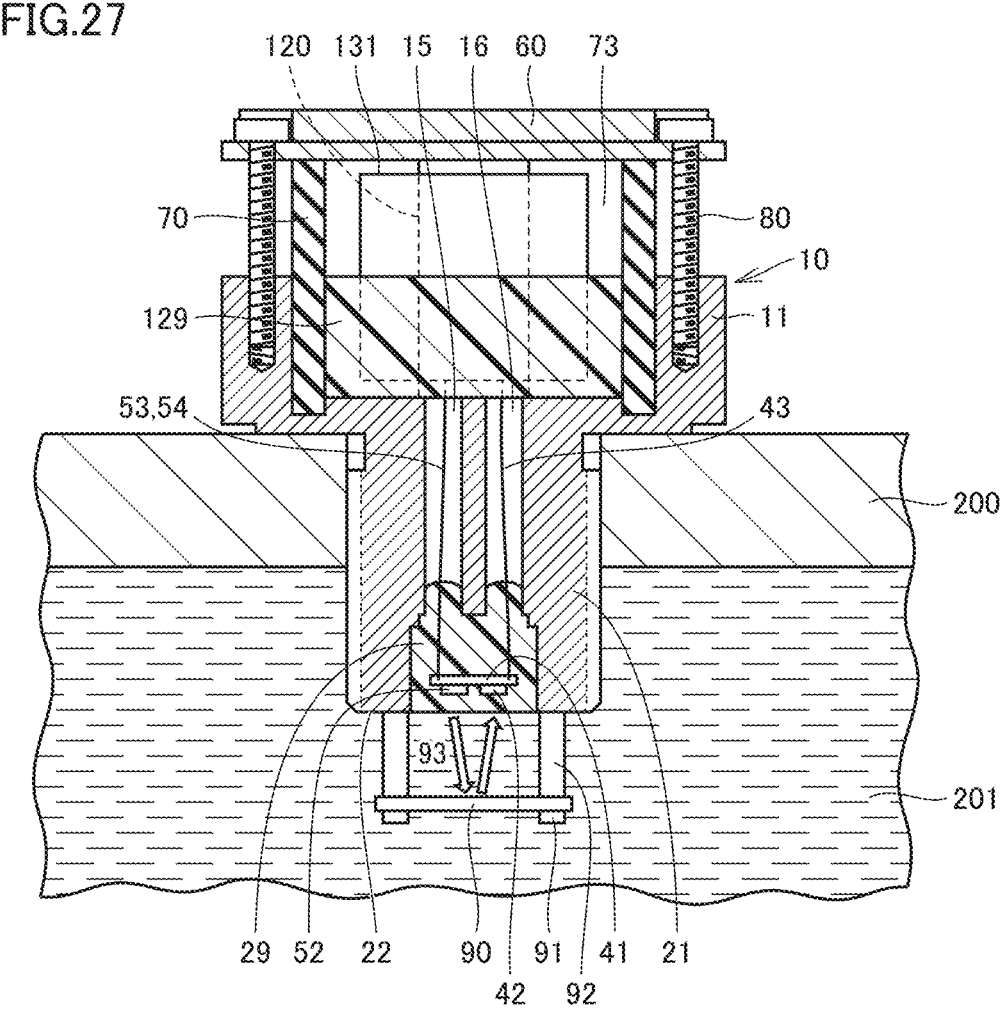
FIG. 27 is a cross-sectional view of an optical sensor according to the third embodiment.

FIG. 27 is a cross-sectional view of an optical sensor 1 according to the third embodiment. According to optical sensor 1 in each of the first and second embodiments having been described above, accommodation space 73 inside heat insulating member 70 is provided as a hollow space, but accommodation space 73 may contain a resin as shown in FIG. 27. In the third embodiment, a part of substrate 131 is sealed by sealing resin 129.

In the embodiment shown in FIG. 27, a resin is contained only in a part of accommodation space 73, but a resin may be contained in the entire accommodation space 73 so as to entirely seal substrates 131.

Sealing resin 129 for partially or entirely sealing substrate 131 is provided, so that the strength for fixing substrate 131 is improved. Thereby, also when the machine equipped with optical sensor 1 vibrates or suddenly operates, substrate 131 can be reliably kept held.

In the embodiments having been described above, fixing member 10 and cover member 60 are integrated with each other using a plurality of bolts 80, without being limited thereto. An integrating member may have any configuration as long as the integrating member is provided separately from a heat insulating member and can integrate fixing member 10 and cover member 60 with each other. For example, fixing member 10 and cover member 60 may be integrated with each other using a caulking member caulked to both head portion 11 of fixing member 10 and cover member 60.

The above explanation includes the features described below.

Japanese Patent Laying-Open No. 2014-8569 discloses a thermoelectric power generation element configured to convert the temperature difference between the temperature of the heated lubricating oil and the surrounding temperature into electric power. A fixing portion is connected to the heat input surface of the thermoelectric power generation element via a heat conducting member. The fixing portion is in contact with the lubricating oil and transfers the heat of the lubricating oil to the thermoelectric power generation element. The thermoelectric power generation element has a heat dissipation surface to which a heat dissipation member is connected. A cover made of a heat insulating material is fixed to the fixing portion and the heat dissipation member so as to cover the thermoelectric power generation element.

Japanese Patent Laying-Open No. 2014-8569 discloses that the cover is fixed to the fixing portion and the heat dissipation member with a bolt. The fixing portion and the heat dissipation member each are formed of a metal material with high thermal conductivity. The cover is formed of a heat insulating material. The fixing portion and the heat dissipation member are different in thermal expansion coefficient from the cover. Thus, fixation of the cover may be loosened, for example, by vibrations of the entire apparatus, which may lead to insufficient strength.

The object of the features described below is to provide a thermoelectric power generation apparatus in which a higher-temperature side heat conducting member and a lower-temperature side heat conducting member can be firmly fixed, thereby providing sufficient strength.

(Feature 1)

A thermoelectric power generation apparatus includes: a higher-temperature side heat conductor; a lower-temperature side heat conductor disposed at a distance from the higher-temperature side heat conductor; a thermoelectric power generation module including a higher-temperature side electrode that is in thermal contact with the higher-temperature side heat conductor, and a lower-temperature side electrode that is in thermal contact with the lower-temperature side heat conductor; a heat insulating member disposed between the higher-temperature side heat conductor and the lower-temperature side heat conductor, the heat insulating member accommodating the thermoelectric power generation module; and an integrating member provided separately from the heat insulating member. The higher-temperature side heat conductor and the lower-temperature side heat conductor are integrated with each other by the integrating member with the heat insulating member interposed therebetween.

By arranging the heat insulating member between the higher-temperature side heat conductor and the lower-temperature side heat conductor, a temperature difference reliably occurs between the higher-temperature side heat conductor and the lower-temperature side heat conductor. Thus, the thermoelectric power generation apparatus can convert this temperature difference into electric power. Also, the higher-temperature side heat conductor and the lower-temperature side heat conductor are integrated with each other by the integrating member that is provided separately from the heat insulating member. Accordingly, the higher-temperature side heat conductor and the lower-temperature side heat conductor can be firmly fixed, so that the strength of the thermoelectric power generation apparatus can be improved.

(Feature 2)

The thermoelectric power generation apparatus according to feature 1, in which the integrating member has electrical insulation performance.

When the thermoelectric power generation apparatus constitutes a wireless communication circuit, the integrating member formed to have electrical insulation can suppress deterioration in wireless communication quality caused by interference of radio waves with the integrating member.

(Feature 3)

The thermoelectric power generation apparatus according to feature 1 or 2, in which the integrating member includes a bolt configured to fasten the higher-temperature side heat conductor and the lower-temperature side heat conductor so as to be integrated with each other.

In this way, the higher-temperature side heat conductor and the lower-temperature side heat conductor are integrated with each other using a bolt. Accordingly, the higher-temperature side heat conductor and the lower-temperature side heat conductor can be firmly fixed, so that the strength of the thermoelectric power generation apparatus can be improved.

(Feature 4)

The thermoelectric power generation apparatus according to any one of features 1 to 3, in which one or each of the higher-temperature side heat conductor and the lower-temperature side heat conductor has a bolt shape.

In this way, the heat conductor having a bolt shape can be fastened to another configuration such as a housing of a machine so as to be fixed. The higher-temperature side heat conductor receives heat from this another configuration or the lower-temperature side heat conductor emits heat to another configuration, so that a temperature difference can be reliably caused between the higher-temperature side heat conductor and the lower-temperature side heat conductor.

(Feature 5)

The thermoelectric power generation apparatus according to any one of features 1 to 4, further comprising a substrate disposed between the higher-temperature side heat conductor and the lower-temperature side heat conductor.

The substrate constituting a power supply circuit or a wireless communication circuit is disposed between the higher-temperature side heat conductor and the lower-temperature side heat conductor, so as to be accommodated inside the heat insulating member together with the thermoelectric power generation module. Thereby, the thermoelectric power generation apparatus can be reduced in size.

(Feature 6)

The thermoelectric power generation apparatus according to feature 5, further comprising a sealing resin for partially or entirely sealing the substrate.

The fixing strength of the substrate is improved by partially or entirely sealing the substrate with the sealing resin, so that the reliability of the thermoelectric power generation apparatus can be improved.

(Feature 7)

The thermoelectric power generation apparatus according to any one of features 1 to 6, further comprising a heat conducting member disposed between the higher-temperature side heat conductor and the lower-temperature side heat conductor, the heat conducting member being in contact with one of the higher-temperature side heat conductor and the lower-temperature side heat conductor and also in contact with the thermoelectric power generation module.

The higher-temperature side heat conductor and the lower-temperature side heat conductor may be in direct contact with the thermoelectric power generation module, but may be in contact with the thermoelectric power generation module through the heat conducting member. In this way, the flexibility of arrangement of the higher-temperature side heat conductor and the lower-temperature side heat conductor can be improved. When a substrate is disposed between the higher-temperature side heat conductor and the lower-temperature side heat conductor, by adjusting the dimensions of the heat conducting member, a space in which the substrate can be accommodated can be reliably formed between the higher-temperature side heat conductor and the lower-temperature side heat conductor.

It should be understood that the embodiments disclosed herein are illustrative and non-restrictive in every respect. The scope of the present invention is defined by the terms of the claims, rather than the description above, and is intended to include any modifications within the meaning and scope equivalent to the terms of the claims.

REFERENCE SIGNS LIST 1 optical sensor, 10 fixing member, 11 head portion, 12, 24, 73 accommodation space, 13, 26 screw hole, 14 recess portion, 15, 16 wiring line through hole, 17 fixing hole, 18, 65 annular groove, 21 thread portion, 22, 31 distal end face, 23, 33, 93 oil infiltrating space, 25 diameter increasing space, 29, 129 sealing resin, 30 holding member, 32 proximal end face, 34 hole, 35 diameter increasing portion, 36 light receiving element support portion, 37 light emitting element support portion, 38 light receiving element accommodating hole, 39 light emitting element accommodating hole, 40 light receiving element module, 41, 51, 102, 103, 131, 132 substrate, 42 light receiving element, 43, 53, 54, 111, 112 wiring line, 45 light receiving/light emitting element module, 50 light emitting element module, 52 light emitting element, 60 cover member, 61 first surface, 62 second surface, 64 through hole, 66 island-shaped portion, 70 heat insulating member, 71 one end, 72 the other end, 80, 91 bolt, 90 reflective member, 92 spacer, 100 thermoelectric power generation unit, 101 thermoelectric power generation module, 104, 105 electrode, 108 p-type thermoelectric conversion element, 109 n-type thermoelectric conversion element, 120 pillar member, 133, 134 electronic component, 140 attachment member, 200 housing, 201 lubricating oil.

The invention claimed is:

1. An optical sensor comprising:
   a light source configured to emit light;
   a light detector configured to receive the light emitted from the light source, an optical path from the light source to the light detector extending through an oil infiltrating space as a space into which oil infiltrates;
   a light source substrate on which the light source is mounted;
   a light detector substrate on which the light detector is mounted;
   an installable holder configured to accommodate the light source substrate and the light detector substrate, the holder including the oil infiltrating space;
   an accommodation member including an accommodation space in which the installable holder, which accommodates both the light source substrate and the light receiver substrate, is installably inserted inside; and
   a sealing resin contained in the accommodation space and sealing the substrates.

2. The optical sensor according to claim 1, wherein the light source and the light detector face each other with the oil infiltrating space of the installable holder interposed therebetween.

3. The optical sensor according to claim 2, wherein the light source and the light detector each have oil-tightness.

4. The optical sensor according to claim 1, further comprising:
   a reflector disposed in the oil infiltrating space and configured to reflect the light emitted from the light source; and
   a plurality of spacers disposed in the oil infiltrating space and configured to space apart the reflector from the sealed accommodation space,
   wherein the light detector is configured to receive the light reflected by the reflector.

5. The optical sensor according to claim 4, wherein the light source and the reflector face each other with the oil infiltrating space interposed therebetween, and
   wherein the light detector and the reflector face each other with the oil infiltrating space interposed therebetween.

6. The optical sensor according to claim 1, further comprising:
   a thermoelectric power generator configured to supply electric power to the light source and the light detector.

7. An optical sensor comprising:
   a light source configured to emit light;
   a light detector configured to receive the light emitted from the light source, an optical path from the light source to the light detector extending through an oil infiltrating space as a space into which oil infiltrates;
   a substrate on which one or both of the light source and the light detector is or are mounted;
   an accommodation member including an accommodation space in which the substrate is accommodated; and
   a sealing resin contained in the accommodation space and sealing the substrate,
   wherein the light source and the light detector each have oil-tightness, and
   wherein the light source and the light detector are exposed to the oil infiltrating space.

* * * * *